United States Patent [19]

Neslund et al.

[11] Patent Number: 5,470,954
[45] Date of Patent: Nov. 28, 1995

[54] ULTRAPURIFICATION PROCESS FOR FACTOR VIII

[75] Inventors: Gerald G. Neslund, Diamond Bar; Shu-Len Liu, Cerritos; Michael J. Griffith, Claremontall, of Calif.

[73] Assignee: Baxter International Inc., Deerfield, Ill.

[21] Appl. No.: 140,695

[22] Filed: Oct. 21, 1993

Related U.S. Application Data

[63] Continuation of Ser. No. 887,387, May 21, 1992, abandoned, which is a continuation of Ser. No. 167,902, Mar. 28, 1988, abandoned, which is a continuation-in-part of Ser. No. 32,800, Mar. 31, 1987, abandoned.

[51] Int. Cl.$^6$ .............................. A61K 35/16; C07K 1/18; C07K 1/22; C07K 14/755
[52] U.S. Cl. ............... 530/383; 530/380; 530/413; 530/414; 530/415; 435/240.27
[58] Field of Search .................... 530/383, 380, 530/413, 415, 414; 435/240.27

[56] References Cited

U.S. PATENT DOCUMENTS

| | | |
|---|---|---|
| Re. 32,011 | 10/1985 | Zimmerman et al. . |
| 3,962,421 | 6/1976 | Neurath . |
| 4,086,218 | 4/1978 | Shambrom et al. . |
| 4,105,650 | 8/1978 | Shambrom et al. . |
| 4,188,318 | 2/1980 | Shambrom . |
| 4,314,997 | 2/1982 | Shambrom . |
| 4,315,919 | 2/1982 | Shambrom . |
| 4,412,985 | 11/1983 | Shambrom . |
| 4,465,624 | 8/1984 | Chiba et al. ............... 530/413 |
| 4,481,189 | 11/1984 | Prince . |
| 4,485,017 | 11/1984 | Tan et al. ............... 530/413 |
| 4,490,290 | 12/1984 | Gani et al. ............... 530/413 |
| 4,511,556 | 4/1985 | Purcell et al. . |
| 4,540,573 | 9/1985 | Neurath et al. . |
| 4,558,006 | 12/1985 | Egrie et al. ............... 530/413 |
| 4,578,335 | 3/1986 | Urdal et al. ............... 530/413 |
| 4,581,231 | 4/1986 | Purcell et al. . |
| 4,591,505 | 5/1986 | Prince . |
| 4,613,501 | 9/1986 | Horowitz . |
| 4,673,733 | 6/1987 | Chandra et al. ............... 530/344 |
| 4,740,306 | 4/1988 | Litwack et al. ............... 530/413 |
| 4,743,680 | 5/1988 | Mathews et al. ............... 530/383 |
| 4,758,657 | 7/1988 | Farb et al. ............... 530/383 |
| 4,765,903 | 8/1988 | D'Andrea et al. ............... 530/351 |
| 4,774,323 | 9/1988 | Newman et al. ............... 530/417 |
| 4,786,726 | 11/1988 | Smith ............... 530/383 |
| 5,214,033 | 5/1993 | Zimmerman et al. ............... 514/21 |

FOREIGN PATENT DOCUMENTS

| | | |
|---|---|---|
| 0150735 | 8/1985 | European Pat. Off. . |
| 61-51000 | 3/1986 | Japan . |
| 2168982 | 7/1986 | United Kingdom . |
| 8501941 | 5/1985 | WIPO . |
| 8600910 | 2/1986 | WIPO . |

OTHER PUBLICATIONS

Fass et al., "Monoclonal Antibodies to Porcine Factor VIII . . . ", Blood, vol. 59(3), pp. 594–600, Mar. 1982.
Goding, "Monoclonal Antibodies: Principle and Practice, Affinity Chromatography and Monoclonal Antibodies", pp. 219–240, Academic Press, 1986.
Hales et al, Methods Enzymology, vol. 70, "Immunochemical Techniques", Part A (Vunakis, Langone, Eds) NY, 1980, pp. 334–355.
Nasrin et al, Eur J Bioch, 161, 1–6, (1986).
Tuddenham et al, J Lab Clin Med 93(1), 40–53, (1979).
Fulcher et al, J Clin Invest., 76, 117–24, (1985).
Muller et al, Biol. Abs., 74(3), p. 1559, Abs 15016, (1981).
Sultan et al, PNAS, 84, 828–31, (1987–Feb.).
Rotblat et al, J Lab Clin Med, 101(5), 736–46, (1983).
Fass et al, Blood, 59(3), 594–600, (1982).
Rotblat et al, Biochem, 24(16), 4294–300, (1985).
Pharmacia Catalog, 1986, pp. 84–89, 92–95, 97–98.
Prave et al., Fundamentals of Biotechnology, pp. 303 to 321, (Jan. 1987).
Biorad Catalog, "Price List L", Jan. 1986, pp. 4–29 and 42 to 48.
Murphy et al., Biochem Biophys Acta, 420, 87–96, (1976).

*Primary Examiner*—Chhaya D. Sayala
*Attorney, Agent, or Firm*—Debra D. Condino

[57] ABSTRACT

A process for purifying Factor VIII:C comprising contacting an immobilized antibody specifically binding a Factor VIII:C with Factor VIII: C, desorbing Factor VIII:C from the antibody which had adsorbed it, eluting Factor VIII:C from the presence of the antibody, passing the eluted Factor VIII:C through an affinity region capable of binding the Factor VIII:C, binding the Factor VIII:C in the affinity region and passing contaminants through said region, and eluting the purified Factor VIII:C.

39 Claims, No Drawings

ULTRAPURIFICATION PROCESS FOR FACTOR VIII

FIELD OF THE INVENTION

This is a continuation application of U.S. patent application Ser. No. 07/887,387, filed May 21, 1992, now abandoned which is a continuation of Ser. No. 07/167,902, filed MAr. 28, 1988, now abandoned which in turn was a continuation-in-part of U.S. patent application Ser. No. 32,800, filed Mar. 31, 1987 now abandoned.

This invention relates to a method of separating and purifying a polypeptide from a complex aqueous mixture. More specifically, the invention relates to such a method in which the polypeptide-containing mixture undergoes a two-step chromatographic adsorption procedure, which procedure comprises an antibody purification step and an affinity region purification step.

BACKGROUND OF THE INVENTION

In recent years, the scientific and medical communities have given increased attention to various polypeptides useful as therapeutic agents and to methods of isolating such polypeptides from the complex source materials in which they are present. An example of such a polypeptide is a blood factor obtained from plasma known as the antihemophilic factor. This blood factor is also identified as Factor VIII procoagulant activity protein (Factor VIII:C). This protein acts to correct the clotting defect in individuals with hemophilia A. It exists in plasma complexed with another protein known as Factor VIII-related protein or Factor VIII:RP. Other designations for Factor VIII:RP are Factor VIII:R:Ag and von Willebrand factor. Because of Factor VIII:C's therapeutic value as a coagulant, it has been regarded as desirable to purify Factor VIII and to isolate Factor VIII:C from Factor VIII:RP. Various procedures have been suggested for the isolation and purification of Factor VIII:C and other polypeptides of therapeutic value. These methods have been generally based on the techniques of immunoaffinity, affinity or ion exchange chromatography. For example, the method in a recent patent for the ultrapurification of Factor VIII:C, Zimmerman & Fulcher, U.S. Pat. No. Re. 32,011, employs such a two-step procedure of affinity and ion-exchange chromatography. Essentially, a Factor-VIII preparation is passed through a column containing agarose beads coupled with mouse monoclonal antibodies directed to Factor VIII:RP. The Factor VIII:C, which is complexed to the von Willebrand factor, is adsorbed onto the matrix while uncomplexed Factor VIII:C moieties and contaminants pass through the column as unbound material. The Factor VIII:C is removed from the bound von Willebrand: antibody complex with a high salt solution containing calcium. The Factor VIII:C solution is desalted and finally adsorbed onto an ion-exchange column, more specifically, agarose beads coupled with positively charged aminohexyl groups. The Factor VIII:C is desorbed from the column with a high salt solution. Although this method is suitable for use in the ultrapurification of a polypeptide, it lacks several important features which would improve the therapeutic safety of the product and facilitate its large-scale production. One distinctive feature of the Zimmerman et al reissue patent is that the monoclonal antibodies are directed to another polypeptide (von Willebrand factor) that is usually in excess and considered associated with the polypeptide of interest (Factor VIII:C). Depending upon the source material, it is possible that as much as 50% of the Factor VIII:C can be in a form not associated with von Willebrand factor. See Amphlett et al, U.S. Pat. No. 4,508,709. The unassociated Factor VIII:C will not be bound by the monoclonal antibodies used in the immunoaffinity step described above, and will consequently be lost in the purification process. To date, there has been no proven advantage for having Factor VIII:C as a product in the uncomplexed form only. Evidence suggests that Factor VIII:C is protected longer from proteolysis by its association with the von Willebrand factor, an important feature when isolating the polypeptide from complex source materials. See Weiss et al, *J. Clin., Invest.* 60, 390–404, 1977. Hence, instead of being a disadvantage, the association of von Willebrand factor with Factor VIII:C could be beneficial insofar as it may confer stability to Factor VIII:C during the purification steps and may extend the half-life of the polypeptide during its therapeutic administration.

Secondly, monoclonal antibodies covalently coupled to any matrix have a tendency to leach, or separate from their matrix and contaminate the final polypeptide-containing product. The patented procedure described above and in the prior art does not guard against the probability of nonhuman cell-derived leached monoclonal antibodies from the immunoaffinity step accompanying and reassociating with the Factor VIII:C during the second ion-exchange step. The high ionic strength buffer used in the immunoaffinity procedure to elute Factor VIII:C is reduced to low ionic strength, which could allow monoclonal antibodies removed from the immunoaffinity column either to rebind to Factor VIII:C or to bind and desorb from the ion-exchange matrix along with the Factor VIII:C.

Thirdly, the desalting process required for the polypeptide-containing solution prior to loading onto the ion exchange column is usually accomplished by large volume dilution, dialysis, or ultra-filtration molecular washing. These methods are not only cumbersome for large-scale production volumes, but inevitably lead to loss of product.

Finally, the aqueous source materials in which the polypeptides of interest are found often are contaminated with one or more viruses. There are techniques for inactivating viruses in polypeptide mixtures, but attempts to combine such techniques with known polypeptide purification processes have produced methods with a multiplicity of steps unsuitable for large-volume production. The methods have also frequently been only partially successful in purifying the polypeptide. For example, in the prior art, a number of viral-inactivating agents have been shown effective for inactivating viruses. The agents have, however, been either denaturing or difficult to separate from the polypeptide of interest, and have required a special treatment or separation step. Other conventional methods for treating polypeptide-containing preparations for potential viral contamination, such as heat or irradiation, have resulted in either significant denaturation of the polypeptide of interest and/or insufficient inactivation of viruses.

The use of viral inactivating agents described herein can inactivate viruses without adversely affecting the biological activity of the polypeptide of interest. Treatment of the aqueous source materials with the viral inactivating agents, accompanied by the other procedures of this invention, produces a final product substantially free of viruses as well as viral inactivating agents.

It is a principal object of this invention to provide a purification process for polypeptides particularly adapted to large-scale purification of a polypeptide with a low level of polypeptide denaturation. It is another object of the invention to provide a polypeptide purification process which is also effective in reducing antibody and viral contamination of the purified product. One additional object of this invention is the development of a process for purifying a polypeptide, free of contaminating substances such as other proteins, viruses, and treating agents used in the purification steps.

SUMMARY OF THE INVENTION

In accordance with the present invention, there is disclosed a process for the isolation and purification of a polypeptide from a complex aqueous mixture. As a result of the process, the polypeptide is substantially free of other contaminating proteins, and is further highly purified by comparison to its purity in the starting aqueous mixture. One preferred embodiment of this process is the inclusion in the process of a technique for reducing the level of pathogenic substances such as viruses. The method comprises purifying a polypeptide in a mixture of polypeptides and other constituents comprising subjecting said polypeptide in said mixture to the following multiple-stage purification process:

(a) immobilizing an antibody which binds by hydrophobic or hydrophilic attraction to the specific polypeptide to be purified, to a substrate before or after said polypeptide is added to said antibody, thereby adsorbing said polypeptide in an immunoaffinity matrix;

(b) eluting the polypeptide from the immobilized antibody by treating the polypeptide:immunoaffinity matrix with a desorbing substance to desorb the polypeptide from said matrix;

(c) passing the polypeptide to be purified through an affinity region capable of binding to the polypeptide through an attraction opposite to that of the antibody in (a) above, thereby binding the polypeptide to the affinity material while allowing contaminants to pass through the affinity region;

(d) wherein the polypeptide-desorbing substance mixture is passed from the first purification region to the second without further modification or alteration of said polypeptide-desorbing substance mixture; and (e) eluting the purified polypeptide from the affinity region. A preferred embodiment comprises incorporating into the above process a virus-inactivating agent comprising an organic solvent and a detergent, followed by removal of said solvent and detergent. This is advantageously done by purifying a polypeptide in a complex aqueous mixture contaminated with lipid-enveloped viruses by:

(a) mixing the complex aqueous mixture with a virus-inactivating agent containing an organic lipid-dissolving or disrupting solvent and a detergent at any stage in the process;

(b) passing the polypeptide mixture through an immunoaffinity matrix containing active immobilized monoclonal antibody specific to the polypeptide and which binds by hydrophobic or hydrophilic attraction to said polypeptide, thereby causing the polypeptide to adsorb to the immunoaffinity matrix;

(c) washing the immunoaffinity matrix with a buffer to remove at least a portion of contaminants from the complex aqueous mixture, while leaving the polypeptide adsorbed to the immunoaffinity matrix;

(d) eluting the polypeptide from the immunoaffinity matrix with an eluting substance, thereby forming a polypeptide:eluting substance mixture to be purified;

(e) passing the polypeptide to be purified through an affinity matrix, thereby causing the polypeptide to bind thereto, while allowing any leached monoclonal antibodies, detergents and other contaminants to pass through the affinity matrix;

(f) wherein the polypeptide to be purified is passed from the first purification region to the second without further modification or alteration of the polypeptide:eluting substance mixture; and (g) eluting the second region with an eluting solution to desorb the polypeptide to form a solution substantially free of contaminants.

DETAILED DESCRIPTION OF THE INVENTION

The present invention is directed to a method of isolating and purifying polypeptides from a complex aqueous mixture. The polypeptides of interest are principally those for human therapeutic administration, research purposes and diagnostic use. Blood plasma proteins are of particular interest. The blood fibrinolysis- and coagulation-promoting factors constitute one preferred group of polypeptides for use in this invention. Representative examples include enzymes such as urokinase, streptokinase, and fibrolase, useful as plasminogen activators, and blood factors such as Factor II, Factor V, Factor VII, Factor VIII, Factor IX, Factor X, Factor XI, Factor XII, Protein C and Protein S, useful as other therapeutic agents. A particular polypeptide of interest is the blood factor Factor VIII, and more particularly Factor VIII:C and Factor VIII coagulation factor antigen. By the process of this invention, such polypeptides can be isolated from complex mixtures such as blood plasma, plasma fractions, commercial concentrates, and tissue culture media, including such media containing synthetically produced polypeptides as well as naturally occurring polypeptides. The process of the invention produces a polypeptide substantially free of contaminants which were present in the mixture before processing as well as those added to the mixture during the processing steps disclosed below. Examples of contaminants include pathogenic viruses, both lipid-enveloped viruses and non-enveloped viruses, pyrogens, leached antibodies, organic solvents, detergents, desorbing agents and other proteins present in the complex mixture from which the polypeptide of interest is isolated.

In accordance with one embodiment of the process of this invention, a complex aqueous mixture containing a polypeptide of interest is added to an anti body which binds to the specific polypeptide to be purified. At the time the antibody binds to the polypeptide, the antibody can be unattached to any other matrix, or it can be, prior to its binding to the polypeptide, bound to a matrix which immobilizes the antibody and fixes it within a predetermined region. A preferred type of region within which the antibody can be fixed is beaded resin in a chromatography column or radial flow cartridge. Whether or, not the antibody is immobilized in a region before its binding to the polypeptide, it is important that the antibody be in an immobilized state at some point after the binding of antibody to polypeptide.

The antibody can be any antibody which is capable of being fixed to an immobilized matrix and able to bind to the polypeptide to be purified. Both polyclonal and monoclonal antibodies can be used, as well as mixtures of either type designed to bind with a number of immobilized substrates or polypeptides or both. Because of their specificity and ready availability in large quantities, monoclonal antibodies are preferred. The choice of antibody will depend upon the polypeptide and immobilized substrate chosen. A preferred class of antibodies useful herein with other preferred operating conditions are those which interact with the polypeptide through hydrophobic interaction if the immunoaffinity step is coupled to a second ion-exchange chromatography step. Antibodies interactive with a polypeptide through hydrophilic interaction can be equally preferred and useful if the immunoaffinity step is coupled to a second hydrophobic interaction chromatography step.

A preferred method of this invention comprises binding the polypeptide to a monoclonal antibody specific to the polypeptide of interest after the antibody has itself been immobilized in an immunoaffinity chromatography column. The mixture of polypeptides is passed through the immunoaffinity chromatography column on which have been immobilized monoclonal antibodies specific to the polypeptide of interest. As the mixture passes through the column or cartridge, the polypeptide adsorbs to the immobilized monoclonal antibodies. The column or cartridge is washed with an aqueous buffer. The buffer removes a major or portion of the virus-inactivating agent, as well as other contaminants, from the complex aqueous mixture, but leaves the polypeptide of interest adsorbed on the column or cartridge. The polypeptide in the column is desorbed and eluted with a desorbing agent. Selection of desorbing agents is within the skill of the art. Preferred desorbing agents for antibodies with hydrophobic attraction to the polypeptide are low ionic strength, low polarity buffered solutions. Low ionic strength usually refers to solutions having an ionic strength, $\mu$, less than 0.2. Examples of salt solutions with low ionic strength include 0.15M sodium chloride, 1.0 mM calcium chloride, and 40 mM calcium chloride. Examples of nonpolar agents which provide low polarity solutions include ethylene glycol, dioxane, propylene glycol and polyethylene glycol. The buffer desorbs the polypeptide, thereby forming a low ionic strength, low polarity polypeptide solution. For antibodies with hydrophilic attraction to the polypeptide, preferred desorbing agents are high ionic strength, aqueous buffered solutions such as 0.8M sodium chloride and 0.25M calcium chloride. High ionic strength refers to solutions having an ionic strength value, $\mu$, above 0.2.

The complex aqueous mixtures that provide a source of the polypeptides of interest often are contaminated by pathogenic viruses, especially lipid-enveloped viruses such as the hepatitis B virus, non-A and non-B hepatitis virus, and HIV (HTLV-III) virus. In the broadest applications of this invention, the immunoaffinity purification combined with the affinity purification, substantial quantities of virus are removed. When one of the preferred embodiments is employed by treating the polypeptide with an organic solvent and detergent, the levels of lipid-enveloped viruses are usually reduced below a detectable level. The operable components of this treatment are the organic solvents and the detergent. Organic solvents are those active in dissolving or disrupting the lipid-containing envelope surrounding many viruses and which do not denature the polypeptide to be purified. Examples include di- and trialkyl phosphates such as di-(n-propyl) phosphate and tri-(n-butyl) phosphate, ethers such as ethyl ether and propyl ether, esters such as amyl acetate, and alkylated and hydroxylated materials such as butylated hydroxyanisole (BHA) and butylated hydroxytoluene (BHT). Mixtures of the above or other organic solvents are also useful. Ethyl alcohol and ethyl ether have been found to be particularly acceptable as have the alkyl phosphates.

Detergents useful herein can be chosen from any of the recognized groups of anionic, cationic and nonionic detergents. Examples include a number of sulfated alcohols and sodium acid salts such as sulfated oxyethylated alkylphenol (Triton W-30 and Triton X-100)), sodium dodecylbenzenesulfonate (Nacconol NR), sodium 2-sulfoethyl oleate (Igepon A), sodium cholate, sodium deoxycholate, sodium dodecylsulfonate, dodecyldimethylbenzylammonium chloride (Triton K-60), oxyethylated amines (Ethomeen), N-dodecylaminoethanesulfonic acid, ethylene oxide-propylene oxide condensates (Pluronic copolymers), polyoxyethylated derivates of esters (Tween 80 and Polysorbate 80), polyoxyethylene fatty alcohol ethers (Brij 35), Nonidet P-40 and Lubrox PX.

The amounts of organic solvent and detergent used in the practice of the preferred embodiments of this invention can vary, depending upon the aqueous mixture to be treated, and upon the solvent or detergent chosen. If ethers or alcohols or mixtures thereof are used, the amount can be from 1 to 50%, preferably from about 5 to 25% by weight of the aqueous mixture if that mixture is blood plasma or blood compositions. The alkyl phosphates are used in concentrations from 0.01 mg/ml of mixture treated to 1.0 g/ml, preferably between about 0.1 mg/ml and 10 mg/ml. The amount of detergent or wetting agent used is not critical. Its function is to improve the contact between the organic solvent and the virus. For many of the nonionic materials useful herein, the wetting agent can comprise from 0.001% to 10%, preferably from 0.01 to 2%, of the aqueous mixture, depending upon the amount of fatty material in the treated aqueous mixture. The amounts of solvent and detergent will also vary depending upon each other, upon the aqueous mixture being treated and the polypeptide to be purified.

The prior art has taught the addition of organic solvents and detergents to concentrated solutions of polypeptides to disrupt and inactivate lipid-enveloped viruses while preserving the protein structure of the desired polypeptide. See U.S. Pat. No. 4,540,573. Organic solvents containing either Tween-80 or Triton X-100 have been shown to be effective reagents for killing viruses found in concentrated solutions of certain proteins without adversely affecting the bioactivity of the proteins. The use of such solvent-detergent mixtures, however, has been avoided because subsequent removal of the mixture from the concentrated protein has proven to be very difficult. See, for example, Prince, A.M. et al., Lancet, p. 706, Mar. 29, 1981. As a result, other detergents, such as sodium cholate or sodium deoxycholate, are more commonly used. These detergents can be removed from the polypeptide of interest by gel exclusion chromatography on, for example, Sephadex G-25. A drawback to the use of these detergents, however, is that they are strong protein denaturants which can adversely affect the bioactivity of the polypeptide. Such detergents can be used herein in amounts which will not denature the polypeptide to be purified, either in combination with other detergents or with protein stabilizers or both.

The disadvantages of the methods of the prior art methods have been overcome by the preferred embodiments of the present invention. The present invention provides a means for the effective removal of virus-inactivating reagents from the polypeptide of interest, thus overcoming the obstacle to the use of detergents such as Tween 80 and Triton X-100 with an organic solvent. In the method of the present invention, the virus-inactivating agents are added to the complex aqueous material containing the polypeptide of interest. As described in greater detail below, the mixture then can be directly applied to a matrix which contains active immobilized monoclonal antibodies to the polypeptide. The polypeptide is adsorbed by the matrix, and the virus-killing reagents can be removed by extensive washing of the matrix.

The matrix can be an immunoaffinity chromatography column which contains a solid support matrix to which active monoclonal antibodies, able to specifically adsorb the polypeptide of interest, are coupled. The monoclonal antibody can be added to the resin support, which frequently has been activated with an activator such as cyanogen bromide. The support is made in accordance with conventional procedures and may comprise, for example, beaded agarose, cellulose, nylon or polyvinyl membranes. As mentioned above, the immunoaffinity matrix is usually in the form of a chromatographic column or cartridge. The preparation of such columns and cartridges is well within the skill of the art. Such columns or cartridges containing an appropriate support can be flushed with water and then equilibrated with the same buffer solution as the aqueous mixture containing the polypeptide to be purified.

The column then is washed with an aqueous buffer to remove a major portion of the virus-inactivating agent and other contaminants which may be non-specifically bound to the monoclonal antibody matrix or to the polypeptide without eluting the polypeptide adsorbed to the column.

The prior art, Livingston, D. M., *Methods in Enzymology*, 34, 723–731, (1974), has suggested that the non-specific binding of contaminants to the polypeptide of interest or the solid support matrix by ionic interaction can be minimized by using high ionic strength solutions or detergents. This has not proved to be a practical suggestion, for the addition of high ionic strength solutions and/or detergents to a conventional matrix often causes the polypeptides bound to the matrix to become unstable or causes a poor rate of adsorption of the polypeptide to the matrix.

In the present process, however, high ionic strength polypeptide solutions containing detergent have been shown not to produce any adverse effects during the immunoadsorption step when using monoclonal antibodies with hydrophobic attraction for the polypeptide. For example, the Factor VIII:C polypeptide from several source material solutions with high ionic strength, e.g. 0.5 to 1.5M NaCl, were found to adsorb to an immunoaffinity matrix at a faster rate than with polypeptide solutions with low ionic strength, e.g. 0.15M NaCl. Factor VIII:C is stable in such source solutions containing an organic sol vent and detergent as well. When the complex aqueous mixture containing the polypeptide of interest and the virus-inactivating agents is added to the column, the polypeptide is adsorbed by the column and its constituents. Other elements of the mixture pass through the column.

After the immunoaffinity chromatography column has been sufficiently washed with the buffer that a major portion of the virus-inactivating agents and other contaminants have been removed from the polypeptide bound to the column, the column is treated with an agent which will release the bound polypeptide. The agent desirably is a polarity-reducing buffer with low ionic strength when the monoclonal anti body has a hydrophobic attraction for the polypeptide. It has been found that using a low polarity, low ionic strength buffer to elute the polypeptide from the immunoaffinity column is advantageous, for the resulting polypeptide solution can be added without modifications to an ion exchange or other affinity matrix.

A major concern in conventional immunoaffinity purification has been the leaching of non-human monoclonal antibodies into the polypeptide eluate solution during the elution step. In the prior art, it is a common practice to change the pH, polarity, or ionic strength of the eluted polypeptide solution so that proper adsorption of the polypeptide to a second affinity region matrix can take place. Usually this alteration is sufficient to cause the leached monoclonal antibodies either to reassociate with the polypeptide or to bind to the second affinity matrix along with the polypeptide and thereby contaminate the final product. In the present process, however, the composition of the solution which desorbs the polypeptide from the immunoaffinity column does not need to be altered prior to the loading of the ion-exchange column. It therefore is more difficult for any monoclonal antibodies which may be present in the solution to rebind to either the polypeptide of interest or the second affinity matrix.

When the low polarity buffer solution is passed through the affinity matrix, the polypeptide binds to the affinity matrix and the solution, while any leached monoclonal antibodies, detergents or other contaminants pass through the column. The affinity matrix is preferably an ion-exchange column which comprises a matrix covalently coupled with charged chemical groups that are able to bind charged biological molecules under low ionic strength and release them as the pH or ionic strength changes. However, if hydrophobic interaction material is used, then the affinity matrix contains nonpolar chemical groups that are able to adsorb the uncharged regions of the polypeptide molecules under high ionic strength. Suitable affinity materials include those chemical functional groups having no substantial affinity for antibodies. Examples of ionic chemical species include aminoalkyl anion exchangers, especially those where the alkyl groups have up to six carbon atoms and cation exchangers. Quaternary aminoethyl, aminoethyl and diethylaminoethyl compounds constitute one preferred class of anion-exchanging moieties. Sulfopropyl and carboxymethyl are acceptable and preferred cation-exchanging moieties. Examples of hydrophobic interaction chemical species are phenyl and n-octyl functional groups. The affinity adsorbent support can be any of the commonly used supports such as fibers, beads, discs or platelets of crosslinked cellulosic material, beaded agarose and the like.

The matrix is then washed to remove remaining traces of contaminating residues on the polypeptide. The washing should be sufficient to reduce contaminants to a level non-toxic to humans, as well as to a level where they do not affect the efficacy of the polypeptide being purified. The washing solution preferably contains the same components as the eluting solution, but at a higher pH and/or lower ionic strength if an anion-exchange matrix with positively charged groups is used. As a general guideline, the elution solution should be buffered with a composition to provide a sufficiently high ionic strength and/or low pH to desorb the polypeptide from an anionic exchange matrix. The solution must be compatible with the polypeptide, be non-toxic, and be able to disrupt the polypeptide affinity matrix bond.

The solution containing the eluted polypeptide can be directly diluted into a buffered solution to produce a purified product suitable for therapeutic use. The solution typically comprises physiological concentrations of salts and human albumin along with nontoxic reagents such as amino acids, acetate, phosphate and citrate, imidazole, trimethamine and the like, that provide a buffering capacity of about pH 7.

The source material for the polypeptide to be purified includes plasma or plasma-derived fractions, for example, cryoprecipitate, suitably solubilized, which contain the polypeptide to be purified. Human plasma or plasma from other animals may also be used in this invention. Other source materials useful in this invention include human or animal tissue culture media containing a polypeptide produced by recombinant DNA technology.

To use cryoprecipitate in this invention, the cryoprecipitate can be dissolved by suspension in an aqueous solution containing components required to provide a reasonably stable environment for polypeptide activity. Such solution components include salts to maintain a suitable ionic strength. After suspension and thorough mixing of the cryoprecipitate in the aqueous solution, it is often desirable to remove insoluble material by such physical techniques as centrifugation or filtration. Adjustments to the cryoprecipitate solution, for example, pH, salts, and PEG addition, can also be made to facilitate the removal of insoluble material. The result is a particle-free solution with stable polypeptide activity. Other source materials may not require adjustments.

A second step can involve the addition of organic solvents and detergents to the source material solution to cause inactivation of lipid-enveloped viruses. After mixing of the organic solvent/detergent mixture with source material, the mixture and source material should stand for a sufficient period of time to inactivate lipid-enveloped viruses. The period of time is dependent on the temperature of the source material solution. A minimum of 3 minutes is used when the source material is a cryoprecipitate solution containing 0.3% tri-n-butyl phosphate and 1.0% Triton X-100 at a temperature of 18° C. or greater.

Prior to performing the immunoaffinity purification step, it is desirable to optimize the solution conditions to enhance adsorption of the polypeptide by the immunoaffinity matrix. Such conditions include the addition of salts (e.g. sodium chloride, calcium chloride) in sufficient concentration to disrupt the association of polypeptide with other proteins if the latter are present. Such conditions could also include a pH adjustment to disrupt the association of polypeptide with other proteins. In general, a wide variety of physical and chemical techniques can be employee to optimize polypeptide adsorption by the immunoaffinity matrix. The techniques of choice will be obvious to one experienced in the field once the properties of the antibody preparation and immunoaffinity matrix have been established.

The immunoaffinity purification step in the process can be performed in a variety of ways. The objects of this step are (1) to adsorb polypeptide onto a matrix to which antibody has been first covalently bound, (2) to wash nonspecifically bound material from the immunoaffinity matrix, thereby separating contaminants from the polypeptide to be purified, and (3) to elute the polypeptide from the immunoaffinity matrix in a substantially purified form. The polypeptide-recognition sites on the antibody molecules are preferably always equal to or in excess of the polypeptide concentration so that quantitative adsorption of the polypeptide from the source material solution is possible. When the immunoaffinity matrix is contained in a column, the rate at which the source material is applied is adjusted to allow sufficient time for polypeptide adsorption to occur. When the immunoaffinity matrix is not contained in a column but is instead added to the polypeptide source material, as in a batch reaction, the mixture is stirred for a sufficient time to allow polypeptide adsorption to occur. It is a common practice to determine empirically the amount of time required for adsorption to occur when either reaction mode is used.

The polypeptide is adsorbed to the immunoaffinity matrix, and the immunoaffinity matrix is washed with an aqueous solution to remove nonspecifically bound or retained material from the matrix. Nonspecifically bound or retained material includes such components of the polypeptide source material as proteins, phospholipids, salts, organic solvent, detergent, and pyrogens or virus particles if the latter are present. The composition of the aqueous wash solution is such as to cause the removal of the above-mentioned nonspecifically bound or retained material from the immunoaffinity matrix, to retain polypeptide on the immunoaffinity matrix, and to maintain polypeptide activity. The composition of the aqueous wash solution meeting the above criteria is commonly determined empirically by those experienced in the field as is the amount of aqueous wash solution required to cause the substantial removal of nonspecifically bound or retained material from the immunoaffinity matrix. When the polypeptide is Factor VIII:C, the ionic strength of the wash solution can have a major effect on the degree of purification achieved. This is because a high ionic strength wash solution removes Factor VIII:RP (von Willebrand Factor) from the immunoadsorbed Factor VIII:C. When followed by elution, the dissociation will result in a Factor VIII:C solution high in specific activity.

Following the washing of the immunoaffinity matrix, the polypeptide is eluted with an aqueous solution containing components causing the dissociation of polypeptide from the antibody. The components in the aqueous solution include polar or nonpolar materials which disrupt the noncovalent bonds that otherwise maintain the polypeptide bound to the antibody. The aqueous solution may contain other components which serve to maintain polypeptide activity, for example, calcium chloride and albumin. The components of the aqueous solution and their respective concentrations can be determined once the other parameters of polypeptide type and complex aqueous mixture type have been selected.

A second part of the inventive process is the use of an affinity matrix purification. As stated earlier, in the broader aspects of this invention, either the immunoaffinity purification step or the affinity purification step can precede the other. But some of the most notable benefits of the process are realized by a two-step process where the immunoaffinity purification precedes the affinity purification. After the polypeptide mixture has been added to the affinity matrix, the anionic exchange affinity region is washed with a low-ionic strength buffer solution. The region is then eluted with a buffer salt solution which preferably has a high ionic strength and/or low pH, and components which serve to maintain polypeptide stability, e.g. calcium ions, polyethylene glycol, and albumin. The eluate containing the polypeptide of interest can be collected in a solution which is the equivalent of the eluting solution except that the eluting salt is deleted.

The process of the present invention is further illustrated by the following examples, which are provided for illustrative purposes only and are not to be construed as limiting. The following is a list of the formulations for solutions employed in Examples 1 to 4.

Solution I (Immunoaffinity Equilibration Solution): 0.05M imidazole, 0.8M sodium chloride, 0.05M calcium chloride, 0.3% (v/v) tri (n-butyl) phosphate, 1.0% Triton X-100; pH adjusted to 7.4±0.1 with 6N HCl.

Solution II (Immunoaffinity Wash Solution): 0.05M imidazole, 0.04M calcium chloride, 5.0% (v/v) ethylene glycol; pH adjusted to 6.4±0.1 with 6N HCl.

Solution III (Immunoaffinity Elution Solution): 0.05M imidazole, 0.04M calcium chloride, 40% (v/v) ethylene glycol, 0.1% (1.0 mg/ml) human albumin; pH adjusted to 6.4 with 6N HCl.

Solution IV (QAE-ZetaPrep Wash Solution): 0.05M histidine, 0.15 M sodium chloride, 1.0 mM calcium chloride, 1.0M glycine, 0.1% (w/v) polyethylene glycol 4000, 0.1% human albumin (U.S.P.); pH adjusted to 6.4 with 6N HCl.

Solution V (QAE-ZetaPrep Elution Solution): 0.05M histidine, 0.6±0.1M sodium chloride, 4.0 mM calcium chloride, 0.1% (w/v) polyethylene glycol 4000, 1% human albumin (U.S.P.); pH adjusted to 5.5 to 6.4 with 6N HCl.

Solution VI (Bulk Dilution Solution): 0.05M histidine, 4.0 mM calcium chloride, 0.1% (w/v) polyethylene glycol 4000, 1.0% human albumin (U.S.P.); pH adjusted to 8.2 with 6N HCl.

Solution VII: 0.05M histidine, 0.15M sodium chloride, 4.0 mM calcium chloride, 0.1% (w/v) polyethylene glycol 4000, 1.0% human albumin (U.S.P.), pH adjusted to 7.1±0.1 with 6N HCl.

EXAMPLE 1

A. Preparation of the Anti-Factor VIII:C Monoclonal Antibody Solution

The monoclonal antibody used herein is derived from a hybridoma, which hybridoma was prepared following generally the method of Milstein and Kohler. Following immunization of Balb/c female mice with human Factor VIII:C, the spleen cells of the immunized mice were fused with myeloma cells P-3Ag 8653 from a mouse myleloma and the resultant hybridomas were screened for those supernatants containing antibody which give selective binding to human Factor VIII:C. The desired hybridoma was subsequently cloned and characterized. As a result, a hybridoma with the identification number GI-F8/1.5.6, from Genetics Institute, Cambridge, Massachusetts, was obtained which produces antibody against an epitope on the human Factor VIII:C protein. Not only does this antibody react with human Factor VIII:C obtained from plasma, but it has been found that it also reacts with human Factor VIII:C produced by cells transformed with recombinant DNA coding for human Factor VIII:C. The preparation of the monoclonal antibody used herein was carried out as follows:

Immunization

Female Balb/c mice (obtained from Jackson Labs) are immunized intraperitoneally on day 0 with 25–50 units of Factor VIII obtained as set forth in Example I which had been emulsified in 0.4 ml of complete Freund's adjuvant. On day 21, the mice are reimmunized with the Factor VIII emulsified in incomplete Freund's adjuvant. Subsequent booster immunizations are adminstered at three week intervals.

The sera of the immunized animals is tested three days after each boost for inhibition of Factor VIII cogulant activity by incubating dilutions of the sera with normal pooled plasma at 37° C. for 2 hours. The residual Factor VIII activity is then measured by the chromogenic Factor VIII assay.

Three days prior to fusion, the mice are challenged with a final injection (intravenous or intraperitoneal) of 25–50 units of Factor VIII in phosphate buffered saline.

Cell Fusion

Fusion is carried out in the absence of serum in accordance with the procedure developed by Kohler and Milstein. The spleens from two immunized mice are removed by blunt dissection, cut longitudinally, followed by teasing out the cells on a plate into 2 mls of ice-cold RPMI-1640/Glutamine, plate rinsed once with 2 ml of the same buffer to get residual cells, and placed in 10 ml tubes. The debris is allowed to settle out for about 5 minutes on ice and the cells are washed at 4° C. in 50 ml s RPMI-1640/Glutamine and thereafter suspended in 10 mls of ice-cold RPMI-1640/Glutamine. A count of the cells totaled $2\times10^8$.

Myeloma cells of strain P3Ag8653 maintained in 207 FCS/RPMI ( glutamine, 2-mercapto ethanol, Gentamycin ) are washed at 10° C. in 50 ml RPMI-1640/Glutamine and thereafter suspended in 10 ml of room temperature RPMI-1640.

The spleen and myeloma cells are mixed in a ratio of about 4 spleen cells to every myeloma cell and brought up to 50 ml RPMI-1640/Glutamine and washed at 10° C. The supernatant is aspirated and the pellet resuspended by flicking the tube. The tube is then placed in a beaker containing 37° C. water. One ml of 50% w/w PEG 1500 is added gradually to the tube over ½ minute while stirring the pellet with the tip of a 1 ml pipette. The mixture is allowed to stand 1 ½ minutes at 37° C. with occasional stirring. Five ml of RPMI-1640/Glutamine at 37° C. is gradually added over a three minute period while stirring. An additional 14 ml of RPMI-1640/Glutamine is added over 1 minute. Followed by 30 ml of 20% FCS RPMI-1640/Glutamine. The cell suspension is centrifugated at 20° C. for 8 minutes and the pellet is suspended to $1.5\times10^5$/ml ($1.5\times10^7$ spleen cells/plate/20 ml) input spleen cells/ml in 20% FCS RPMS-1640+HAT. Normal mouse peritoneal cell feeders ($2.5\times10^4$/ml) from the same strain as the spleen cell donor is added. 0.2 ml aliquots were placed drop wise in Costar 96 well places (measure out 20 ml/plate). After 7 days ½–⅔ of the medium is replaced with HAT+RPMI-1640+20% FCS. Between days 12–28 the medium is replaced periodically with HT & RPMI-1640 & 20% FCS (the medium is replaced when the cells began to turn yellow: –2 days). From day 30 on, the medium is replaced with RPMI-1640+20% FCS.

The stock solutions are as follows:

1. HT 200X: hypoxanthine, 136 mg thymidine, 38.8 mg D.D.W., 100 ml dissolved at 70° C., filter sterilized, and stored frozen at –29° C. for about 6 months.
2. Aminopterin 1,000X: aminopterin 3.5 mg 0.10N NaOH, 1 ml D.D.W., 19 ml filter sterilized, stored in dark at –20° C. for –2 months.
3. HAT 1X: HT 100X, 5 ml; Aminopterin 1.000X, 0.5 ml; RPMI+20% FCS, 500 ml
4. HT 1X: HT 100X, 0.5 ml; RPMI+20% FCS, 500 ml
5. Azaguanine 100X: 8-azaguanine 2.5 mg 0.01N NaOH 10 ml filter sterilized, stored in 1 ml aliquots at 20° C.

Screening Hybrid Cell Cultures for Antibodies to Factor VIII:C Hybrid cell cultures are screened for the production of anti-Factor VIII:C antibodies by two methods. 1. Binding assay Microtiter plates (96-well) are coated with rabbit anti-mouse IgG by incubating in 0.2M carbonate buffer, pH 9.5 for two hours at about 37° C. The plates are washed three times with phosphate buffered saline containing 0.05% Tween 20 (PBS/Tween 20). Nonspecific sites were coated by incubating the plates with PBS containing 3% gelatin. Aliquots of hybrid cell supernatant are added to the wells and incubated at 37° C. for two hours and thereafter washed three times with PBS/Tween 20. A plasma-derived fraction of human Factor VIII:C is added and incubated overnight at toom temperature and thereafter washed three times with PBS/Tween 20. Anti-Factor VIII $^{125}$I-FAB' (prepared from IgG isolated from the plasma of a patient with a high titer Factor VIII inhibitor), is added and incubated at 37° C. for four hours and subsequently washed three times in PBS. The wells are cut with a hot wire cutter and a radioactivity count is made. Positives in this assay indicated antibody to Factor VIII:C.

2. Inhibition Assay

Aliquots of hybrid cell supernatant are mixed with equal volumes of normal pooled plasma and incubated at 37° C. for 2 hours. The samples are diluted to obtain a proper assay (chromogenic or clotting assay) of Factor VIII:C bioactivity. A decrease in the Factor VIII:C activity of normal pooled plasma indicates the presence of an inhibitory antibody to Factor VIII:C. This assay does not detect the presence of non-inhibitory antibodies to Factor VIII:C.

Cells wich are positive by either of the above two assays are cloned and subcloned in soft agar in accordance with the technique described herein below. Subcloned cells are then grown in mice as ascites tumors for the production of antibody-rich ascites fluid.

Soft Agar Cloning Technique

1. Prepare 0.5% agar medium:

For 500 ml:

10×Earl's Balanced Salt Solution, 5.5 ml, Mix and warm to 45° C.

RPMI-1640, 434 ml

Heat 50 ml of 5% agar solution to 100° C., and add the heated solution to the RPMI-1640 solution.

Incubate in 45° C. waterbath.

Allow for 18 ml 0.5% agar/plate.

2. Hybrid cell dilutions: for each line use 4 tubes labeled with line's name and marked 1, $8^{-1}$, $8^{-2}$, $8^{-3}$. Dilutions may vary, e.g., $8^{-1}$, $8^{-2}$, $8^{-3}$, $8^{-4}$. To tube 1 add 0 ml, to others 0.7 ml of RPMI-1640. Hybrid cells should be healthy and in the log phase of growth. The cells are suspended and 0.7 ml transferred to tube 1 and 0.1 to tube $8^{-1}$ mixed and 8-fold serial dilutions are carried out by diluting 0.1 ml from the tube $8^{-1}$ into tubes $8^{-2}$, $8^{-3}$ and discarding 0.1 from $8^{-3}$ tube, so all contain 0.7 ml. Place in 37° C. bath. It is preferred that all of these dilutions are used for first cloning. The '1' dilution may usually be omitted for subcloning.

3. 100×15 mm petri dishes are labeled and with a 25 ml disposable pipette 15 ml of 0.5% Bacto-agar medium is pipetted into dishes and allowed to harden for 20 minutes before adding the soft agar overlay containing cells in 0.33% agar medium. It is important not to tilt plates during this period. The remainder of the 0.5% Bacto-agar medium is kept at 45° C.

4. Soft agar overlay: An aliquot of 0.5% agar is poured into a 50 ml plastic tube and placed in a 45° C. water bath in the hood. Tubes containing cells are removed individually from the 37° C. bath. 1.4 ml agar is added with a 5 or 10 ml disposable pipette, pipetted up and down to mix, and most of the mixture (avoiding bubbles) is overlayed onto the 0.5 agar base. It is essential during this step that neither the agar nor cells have cooled, otherwise a homogeneous 0.33% agar mixture will not be obtained.

5. The plates are allowed to harden for 30 minutes without moving (except for sliding in hood) and incubated at 37° C.-5% $CO_2$ for 7–14 days.

6. When discrete colonies appear, clones are 'picked' with sterile pasteur pipettes (i.e., the tip is placed over the colony and sucked up using a clean pipette for each colony), and the cells are placed in 150 ul of 20% FCS/RPMI-1640 in 96 well Costar plates.

7. The plates are incubated at 37° C. 5% $CO_2$ for 7–14 days. When culture supernatant turns yellow, the clones are screened by the defined methods.

Purification of Monoclonal IgG from Ascites Fluid

A. Ascites fluid from Example IV is filtered through glass wool plug to remove particulate matter.

B. The Ascites fluid from (A) is passed through 0.45 micron filter, diluted with an equal volume of 0.02M Tris, pH 8.5 and passed through 0.22 micron filter immediately prior to purification as below.

C. The filtered sample is injected onto a TSK DEAE-SPW HPLC ion exchange column equilibrated at 24° C. in 0.02M Tris, pH 8.5. The flow rate is adjusted to 1.0 ml per minute, and 1-ml fractions are collected. Bound IgG is eluted using a linear gradient from 0% B to 30% B (buffer A is 0.02M Tris, pH 8.5; buffer B is 0.02M Tris, pH 7.0 containing 1.0M NaCl ).

D. Fractions are assayed for inhibition of Factor VIII:C bioactivity by mixing an aliquot of each fraction with appropriately diluted normal pooled plasma prior to analysis in a Factor VIII:C bioassay (as described above).

E. Fractions containing anti-VIII:C antibody are pooled for use as immuno-adsorbent.

The hybridoma, prepared as described above, was procured from Genetics Institute, Inc. of Cambridge, Mass. The cell line as been deposited with the American Type Culture Collection 12301 Parklawn Drive, Rockville, Md. 20852, and has the indentification number ATCC HB 11552.

Monoclonal antibodies (mAb) to human plasma Factor VIII:C are dialyzed against ten volumes of 0.1M sodium bicarbonate, 0.5M NaCl , pH 8.5 (coupling solution) for 4 hours at 2 to 8° C. The dialysis is repeated overnight. The antibody protein concentration, determined by adsorption at 280 nm, is adjusted to 1.1 grams per liter with the coupling solution.

B. Preparation of the Immunoaffinity Resin

The monoclonal antibody is coupled to cyanogen bromide-activated Sepharose CL-2B as described by March et al, *Anal Biochem*, 60, 149–152 (1974). The method is as follows. Sepharose CL-2B, pre-swollen, is washed with ten resin-volumes of deionized water, and suspended in one resin-volume of cold (2°–8° C.) deionized water. Two resin-volumes of 2.0M sodium carbonate are added to the resin and stirred. For each liter of resin, 60 g of cyanogen bromide is dissolved in 120 ml of acetonitrile and added to the resin with vigorous stirring. After 10 to 30 minutes of incubation, depending upon the rate and extent of activation needed, the resin suspension is suction-filtered and washed five times with two resin-volumes of coupling solution. The resin is immediately transferred to a beaker and added to the dialyzed monoclonal antibody solution. The resin suspension is stirred for two hours at 21° C. which produces a coupling efficiency greater than 90% with approximately 1 g of monoclonal antibody bound per liter of resin. The resin suspension is stored overnight in the cold, suction filtered, and washed four times with two resin-volumes of cold coupling solution. The resin is transferred to a beaker containing three resin-volumes of 0.2M glycine, pH 8.0, stirred for two hours at 21° C. to block the remaining reactive sites on the resin, suction filtered, and washed five times with two resin-volumes of a 0.1M sodium acetate, 0.5M NaCl , pH 3.5 solution. The antibody-resin mixture is finally washed four times with two resin-volumes of 10 mM acetic acid, pH 3.5, and stored in one resin-volume of the same solution at 2°–8° C. until needed. The antibody-resin mixture has been found to be functionally active when stored over prolonged periods in the acetic acid solution.

C. Preparation of Factor VIII:C Source Material Solution

Approximately 3000 liters of fresh human plasma is mixed with an anti coagulant, and stored at −25° C. The frozen human plasma is thawed under conditions which result in the formation of 30 kg of insoluble material referred to as cryoprecipitate (cryo) as described by Shanbrom et al. U.S. Pat. No. 3,631,018 (1971). The cryo is collected by centrifugation which separates the cryo from the soluble plasma material. The cryo, whether it had been stored frozen at −70° C. or received fresh at 5° C. is dissolved at 20° to 3° C. in two volumes of distilled water containing 50 uM $CaCl_2$. The pH of the cryo suspension is slowly adjusted to 6.7±0.2 by the addition of 1M acetic acid. The temperature is lowered to 9° C. and held at that temperature until an insoluble material forms over time and is separated from the soluble material by centrifugation. The temperature of the cold supernate (about 75 liters) is increased to 21°C. and the pH adjusted to 7.4±0.1 with 1N NaOH. Sodium chloride (solid) and calcium chloride (5M stock) are slowly added to the cold supernate solution to obtain final concentrations of 0.8M NaCl and 0.05M $CaCl_2$, respectively. Finally, a 3.33 to 1 ratio mixture of Triton X-100 and tri(n-butyl) phosphate (TNBP) is added to the solution as a viral inactivating agent at a final concentration of 1.3% (v/v). The solution thus obtained is referred to as cryoprecipitate-detergent (cryo-detergent) solution.

D. The Immunoaffinity Chromatography Step

Approximately 2.5 liters of the antibody-resin mixture is packed into a column in the presence of 10 mM acetic acid, pH 3.5 at 21°C. The column is washed at 21° C. with 3 to 4 resin-volumes of distilled water followed by equilibration with 3 to 4 resin-volumes of Solution I. Approximately 75 liters of cryo-detergent solution is applied to the column from top to bottom at a flow rate of 2 to 5 liter per hour. The column is washed with 18 resin-volumes of Solution II at a flow rate of 10 liter per hour. The Factor VIII:C polypeptide is eluted off the column in the reverse flow direction by applying about four resin-volumes of Solution III. The flow rate ranges from 2 to 5 liters per hour.

E. The Ion Exchange Chromatography Step The ion exchange matrix, which is a compressed cellulose disk cartridge containing quaternary aminoethyl functional groups (QAE ZetaPrep 250) is conditioned for use by washing the cartridge with the following solutions: 500 ml of 0.15M NaCl, 1 liter of 1.0M acetic acid, 1 liter of 0.1M imidazole, 1.0M NaCl, pH 8.2, eight liters of 0.15M NaCl, and finally two liters of Solution III. After conditioning, the mAb eluate solution containing the Factor VIII:C is loaded onto the QAE ZetaPrep 250 at a flow rate ranging from 0.4 to 1.0 liter per hour. The QAE ZetaPrep cartridge is washed with two liters of Solution IV and Factor VIII:C is eluted with about two liters of Solution V. The eluate is added to 3 volumes of physiologically compatible Solution VI, and further diluted with Solution VII to adjust the final potency of the Factor VIII:C. The ultrapurified Factor VIII:C material is sterile filtered through a 0.2 micron filter, placed in glass vials, frozen, and lyophilized without heat treatment.

EXAMPLE 2

A. Preparation of Factor VIII:C Source Material Solution

Approximately 86 kg of cryoprecipitate derived from plasma as described in Example 1, is stored at −70° C. as a human Factor VIII:C enriched plasma fraction, is dissolved in twice its weight of water and calcium chloride, is added to a final concentration of 50 uM. The pH of the cryosuspension (250 liters) is slowly adjusted to 6.7 with 1M acetic acid. The temperature of the Factor VIII:C solution is gradually cooled to 9.5° C. as a precipitation occurs over a 20-minute period of continuous mixing. The precipitate, which is predominately fibrinogen and fibronectin accounting for about 50% of the total protein, is removed by centrifugation at 3000×g for 15 minutes at 9.5° C. The pH of the resulting cold supernate (225 liters) is adjusted to 7.4 with 1N NaOH, and filtered through a 0.5 to 0.8 micron normal pore size membrane to remove any particles with little loss of Factor VIII:C. To the filtered supernate is added NaCl to 0.8M, $CaCl_2$ to 0.05M, and a Triton X-100/tri-(n-butyl) phosphate mixture (3.3:1 ratio) to 1.3% (v/v) with little loss of Factor VIII:C (17.9 units/ml). This is designated as the cryo-detergent solution.

Immunoaffinity Chromatography Step

The cryo-detergent solution, 230 liters, is applied at room temperature from top to bottom through a vertical column containing 5 liters of the immunoadsorbent (capacity is 1 g mAb per liter resin) at a flow rate of 8.5 liters per hour. The mAb-resin is washed with 40 volumes of Solution II at a flow rate of 20 liters per hour to remove contaminating proteins, viruses, and the virus-inactivating agents.

The resin-bound Factor VIII:C is desorbed from the resin with 19.4 liters of Solution III at a flow rate of 6 liters per hour.

Ion-Exchange Chromatography Step

The Factor VIII:C mAb eluate pool (19.4 liters) is passed directly onto a QAE-ZetaPrep 800 cartridge (LKB, Bromma, Sweden) from the inner core through to the outer peripheral matrix at a flow rate of 1 to 5 liters per hour. The QAE-ZetaPrep matrix is washed with 8 to 10 liters of Solution IV at a flow rate of 4 liters per hour. The Factor VIII:C is eluted from the QAE matrix in a reverse flow direction with 3 liters of Solution V at a flow rate of 3.2 liters per hour, and added to 9 liters of Solution VI. Finally, the potency of Factor VIII:C bulk solution is adjusted with 6.5 liters of Solution VII to produce a highly purified Factor VIII:C suitable for therapeutic use.

EXAMPLE 3

This example demonstrates that increasing the ionic strength of the Factor VIII preparation will increase the rate of Factor VIII:C adsorption to resin coupled with anti-Factor VIII:C monoclonal antibodies which bind to Factor VIII:C through hydrophobic interaction. Results are presented in Table 1.

In the first experiment, cryoprecipitate was dissolved in a solution such that it comprised 9.5 units/ml Factor VIII:C in a solution of 0.03M sodium citrate, 0.12M NaCl, 0.1M glycine, and 1 unit/ml heparin. One ml aliquots of the cryoprecipitate solution, containing Factor VIII:C in the presence of 0.12, 0.52, and 1.0M NaCl, respectively, were each added to 0.1 ml monoclonal antibody-resin and 0.1 ml control resin coupled with normal mouse IgG. With continuous mixing, 0.1 ml aliquots of the resin slurries were centrifuged and assayed for Factor VIII:C activity at time t=0, 0.5, 2.5, and 5 hours.

In the second experiment, Hemofil C (antihemophilic factor, Baxter-Hyland Division) was reconstituted with water such that it comprised 28 units/ml Factor VIII:C in a solution of 0.02M sodium citrate, 0.15M NaCl, 0.10 glycine, 50 uM $CaCl_2$, 1% (w/v) polyethylene glycol, 1% human albumin, pH 7.0. Fourteen ml aliquots of Factor VIII:C solutions containing 0.15M, and 1.0M NaCl, respectively, were each added to 1 ml mAb-resin and 1 ml uncoupled control resin. With continuous mixing, 0.3 ml aliquots of the resin slurries were centrifuged and assayed for Factor VIII:C activity at time t=0, 0.08, 0.25, 0.5, 1.0, 1.5, and 2.0 hours.

In the third experiment, lyophilized mAb-purified Factor VIII:C was reconstituted with water such that it comprised 14 units/ml Factor VIII:C in Solution VII. The rate of Factor VIII:C adsorption to the mAb-resin was determined as described in the second experiment of this example.

TABLE 1

IONIC STRENGTH EFFECT ON THE RATE OF FACTOR VIII: C ADSORPTION TO mAb-RESIN

| Experiment # | Factor VIII Preparations | Final Conc. of NaCl (M) | Relative Factor VIII: C Activity Adsorbed after 1 hr. |
|---|---|---|---|
| 1 | Cryo Solution | 0.12 | 27 |
|   | Cryo Solution | 0.52 | 43 |
|   | Cryo Solution | 1.0 | 53 |
| 2 | Hemofil C, AHF | 0.15 | 54 |
|   | Hemofil C, AHF | 1.0 | 62 |
| 3 | Method M, AHF* | 0.15 | 89 |
|   | Method M, AHF* | 1.0 | 97 |

*Monoclonal antibody-purified Factor VIII: C

EXAMPLE 4

This example demonstrates that the eluted Factor VIII:C material from the antibody-resin composite is highly purified, although retaining a significant portion of Factor VII-I:RP associated with it. A quantity of 1.15 kg of cryoprecipitate was dissolved in twice its weight in water in the presence of 50 uM $CaCl_2$. The pH was adjusted to 6.7 with acetic acid and gradually cooled down to 9.5° C. The precipitation which formed over a 10 minute period was removed by centrifugation at 4,500 xg for 20 min. The pH of the cold temperature supernate was adjusted to 7.4 with 1M NaOH followed by addition of NaCl to 0.8M, $CaCl_2$ to 0.05M, and a 3.3:1 ratio of Triton X-100; tri-(n-butyl) phosphate mixture to 1.3% (v/v). The solution is referred to below as cryo-detergent solution.

Approximately 3 liters of the cryo-detergent solution was applied at room temperature from top to bottom through a 100 ml column of mAb-resin (capacity: 1 mg mAb per ml resin) at a flow rate of 3 ml/min. The column was washed with 1800 ml of Solution II at a flow rate of 10 ml/min. The Factor VIII:C material was eluted off the mAb resin with 450ml of Solution III without human albumin at a flow rate of 5 ml/min. The specific activity of the purified Factor VIII:C was then determined by one-stage clotting assays, and protein concentration derived from absorbance at 280 nm and dye-binding techniques. Table 2 below shows the activity of the Factor VIII:C recovered from the indicated starting material.

TABLE 2

PURIFICATION OF FACTOR VIII: C BY THE IMMUNOAFFINITY METHOD

| STEP | TOTAL ACTIVITY (Units) | VOLUME (ml) | PROTEIN (g) | SPECIFIC ACTIVITY (Units/mg) | PURIFI- CATION | RECOVERY (%) |
|---|---|---|---|---|---|---|
| Human Plasma | 100,000 | 120,000 | 7,000 | 0.014 | 1 | 100 |
| Cryoprecipitate Suspension | 53,800 | 3,450 | 180 | 0.30 | 21 | 54 |
| Cryo-detergent Solution | 52,000 | 3,100 | 84 | 0.62[a] | 44 | 52 |
| Immunoaffinity Eluate | 43,500 | 450 | 0.024 | 1800[b] | 128,000 | 44 |

[a]contains approximately 0.17 Units Factor VIII: RP per Unit Factor VIII: C
[b]contains approximately 0.010 Units Factor VIII: RP per Unit Factor VIII: C

What is claimed is:

1. A method of purifying Factor VIII:C from a mixture of polypeptides and contaminants comprising:

(a) adsorbing an antibody to a matrix to form an immunoaffinity matrix, which antibody binds by hydrophobic attraction to the Factor VIII:C to be purified to form hydrophobic bonds, adding the mixture to said antibody before or after said antibody is bound to the matrix, thereby adsorbing said Factor VIII:C in the immunoaffinity matrix;

(b) eluting the Factor VIII:C from the immobilized antibody by treating the Factor VIII:C:immunoaffinity matrix with a desorbing substance which breaks the hydrophobic bonds between the Factor VIII:C and the immobilized antibody to desorb the Factor VIII:C from said matrix wherein the desorbing substance is a nonpolar agent in a buffered salt solution;

(c) passing the Factor VIII:C to be purified through an affinity region which is an ion-exchange region capable of binding to the Factor VIII:C, thereby binding the Factor VIII:C to the affinity material while allowing the contaminants to pass through the affinity region; and (d) eluting the purified Factor VIII:C from the affinity region.

2. A method according to claim 1 wherein said mixture of polypeptides is blood plasma.

3. A method according to claim 1 wherein said mixture of polypeptides is a blood plasma fraction that has been solubilized.

4. A method according to claim 1 wherein said mixture of polypeptides is present in a cell culture media derived from recombinant DNA technology.

5. A method according to claim 1 wherein said mixture of polypeptides is present in a final product which is to be repurified.

6. A method according to claim 1 wherein said antibody is monoclonal.

7. A method according to claim 1 wherein said matrix comprises a resin.

8. A method according to claim 1 wherein said matrix comprises agarose beads.

9. A method according to claim 1 wherein a washing is employed after the Factor VIII:C to be purified is adsorbed by the immunoaffinity matrix.

10. A method according to claim 9 wherein said washing is carried out with a buffered salt solution.

11. A method according to claim 1 wherein said desorbing substance is a buffered salt solution containing a nonpolar agent.

12. A method according to claim 11 wherein said nonpolar agent is ethylene glycol or propylene glycol.

13. A method according to claim 1 wherein said immunoaffinity matrix is a vertical column, a radial-flow cartridge, or a free mixture of said matrix with Factor VIII:C.

14. A method according to claim 1 wherein the Factor VIII:C is passed through said affinity region before the Factor VIII:C is passed through said immunoaffinity matrix.

15. A method according to claim 1 wherein said affinity region contains resin, agarose beads, or cellulose.

16. A method according to claim 1 wherein said affinity region contains amino diethylaminoethyl or quaternary aminoethyl functional groups as anion exchangers, or sulfopropyl, phospho, or carboxyalkyl functional groups as cation exchangers.

17. A method according to claim 1 wherein said affinity region contains an amino diethylaminoethyl or quaternary aminoethyl functional group deposited on a cellulosic matrix in a cartridge.

18. A method according to claim 1 wherein a washing is employed after the Factor VIII:C is bound to the affinity region.

19. A method according to claim 18 wherein said washing is conducted with a buffered salt solution of low ionic strength.

20. A method according to claim 1 wherein said eluting of Factor VIII:C from the affinity region is conducted with a buffered salt solution of high ionic strength.

21. A method according to claim 1 wherein the eluting of Factor VIII:C from either the immunoaffinity matrix or the affinity region is accomplished by adding the eluting solution to said matrix or region to cause a flow through the matrix or region in a reverse direction from the flow of the polypeptide mixture or Factor VIII:C desorbing substance mixture into the matrix or region.

22. A method according to claim 1 wherein a virus-inactivating step is employed.

23. A method according to claim 22 wherein said virus-inactivating step uses an organic solvent to inactivate the viruses present in the mixture of polypeptides.

24. A method according to claim 23 wherein said organic solvent is a tri-n-alkyl phosphate, dialkyl ether, or amyl acetate.

25. A method according to claim 22 wherein said virus-inactivating step uses a detergent to inactivate the viruses present in the mixture or polypeptides.

26. A method according to claim 25 wherein said detergent is Triton o X-100, Tween 80, sodium cholate, or sodium deoxycholate.

27. A method according to claim 22 wherein said virus-inactivating step uses an organic solvent and a detergent to inactivate the viruses present in the mixture of polypeptides.

28. A method according to claim 27 wherein said organic solvent is a tri-n-butyl phosphate and said detergent is an oxyethylated alkylphenol.

29. A method according to claim 22 wherein said virus-inactivating step is performed prior to the immunoaffinity purification step or the affinity purification step.

30. A process for purifying Factor VIII:C from a complex aqueous mixture contaminated with lipid-enveloped pathogenic viruses, which comprises:

(a) mixing the complex aqueous mixture with a virus-inactivating agent containing an organic lipid-dissolving or disrupting solvent and a detergent at any step in the process;

(b) passing the complex aqueous mixture through an immunoaffinity matrix containing active immobilized monoclonal antibody specific to Factor VIII:C, thereby causing the Factor VIII:C to adsorb to the immunoaffinity matrix by hydrophobic attraction said Factor VIII:C to form hydrophobic bonds;

(c) washing the immunoaffinity matrix with an aqueous buffer to remove at least a portion of contaminants from the complex aqueous mixture, while leaving the Factor VIII:C adsorbed to the immunoaffinity matrix;

(d) eluting the Factor VIII:C from the immunoaffinity matrix with a desorbing substance which disrupts the hydrophobic bonds formed in step (b), thereby forming a Factor VIII:C: desorbing substance mixture wherein the desorbing substance is a non-polar agent in a buffered salt solution;

(e) passing the Factor VIII:C to be purified through an affinity region, thereby causing Factor VIII:C to bind thereto by hydrophilic attraction while allowing any leached monoclonal antibodies, detergents and residual contaminants to pass through the affinity region;

(f) washing the affinity region with an aqueous buffer to remove residual contaminants from the Factor VII-I:C:desorbing substance mixture while leaving Factor VIII:C adsorbed to the affinity region;

(g) eluting the Factor VIII:C from the affinity region with an eluting solution which disrupts hydrophilic bonds between the affinity region and the Factor VIII:C to elute the Factor VIII:C substantially free of contaminants; and (h) wherein the Factor VIII:C to be purified is passed from the immunoaffinity matrix of step (d) to the affinity region of step (e) without further modification or alteration of the Factor VIII:C: desorbing substance mixture 31. A method according to claim 30 wherein said organic solvent in step (a) is tri-(n-butyl) phosphate, and said detergent is Triton X-100.

32. A method according to claim 30 wherein said complex aqueous mixture in step (b) has a high ionic strength comprising sodium chloride ranging from 0.5 to 1.5 molar or calcium chloride ranging from 0.07 to 0.5 molar 33. A method according to claim 30 wherein said aqueous buffer in the step (c) is a low ionic strength buffered salt solution.

34. A method according to claim 30 wherein said desorbing substance in step (d) is a low ionic strength buffered salt solution containing ethylene glycol or propylene glycol, and has a pH ranging from 6.3 to 7.2.

35. A method according to claim 30 wherein said affinity region in step (e) contains amino diethylaminoethyl or quaternary aminoethyl functional groups deposited on a cellulosic matrix in a cartridge.

36. A method according to claim 30 wherein said eluting solution in step (g) is a high ionic strength buffered salt solution containing sodium chloride ranging from 0.6 to 0.8 molar, human albumin ranging from 0.1 to 1 percent, and has a pH ranging from 5.5 to 6.4.

37. A method according to claim 30 wherein the affinity region purification step precedes the immunoaffinity matrix purification step in said process, so that the complex aqueous mixture is first passed through the affinity region, and the Factor VIII:C substantially free of contaminants is subsequently eluted from the immunoaffinity matrix.

38. A method of purifying Factor VIII:C from a mixture of polypeptides and contaminants comprising:

(a) immobilizing an antibody, in a first purification region in an immunoaffinity matrix, which antibody binds by hydrophobic attraction to the Factor VIII:C to be purified to form hydrophobic bonds, adding the mixture to said antibody before or after said antibody is bound to the matrix, thereby adsorbing said Factor VIII:C in the immunoaffinity matrix;

(b) eluting the Factor VIII:C from the immobilized antibody by treating the Factor VIII:C:immunoaffinity matrix with a desorbing substance which is non-polar or of low polarity in a buffered salt solution having a low ionic strength, thereby forming a Factor VIII:C:desorbing substance mixture;

(c) passing the Factor VIII:C to be purified through a second purification region which is an affinity region, said affinity region being an ion-exchange region, thereby binding the Factor VIII:C to the affinity region while allowing contaminants to pass through the affinity region;

(d) eluting the purified Factor VIII:C from the affinity region with a desorbing substance having an ionic strength sufficient to desorb the Factor VIII:C from said affinity region; wherein the Factor VIII:C to be purified is passed from the purification region of step (b) to the purification region of step (c) without further modification or alteration of the Factor VIII:C:desorbing substance mixture.

39. A method according to claim 38 wherein a virus inactivating step is employed before said Factor VIII:C is applied to said immunoaffinity matrix.

* * * * *

(12) REEXAMINATION CERTIFICATE (4267th)
United States Patent
Neslund et al.

(10) Number: US 5,470,954 C1
(45) Certificate Issued: Feb. 6, 2001

(54) ULTRAPURIFICATION PROCESS FOR FACTOR VIII

(75) Inventors: Gerald G. Neslund, Diamond Bar; Shu-Len Liu, Cerritos; Michael J. Griffith, Claremontall, CA (US)

(73) Assignee: Baxter Travenol Laboratories, Inc., Deerfield, IL (US)

Reexamination Request:
No. 90/005,182, Dec. 14, 1998

Reexamination Certificate for:
Patent No.: 5,470,954
Issued: Nov. 28, 1995
Appl. No.: 08/140,695
Filed: Oct. 21, 1993

Related U.S. Application Data

(63) Continuation of application No. 07/887,387, filed on May 21, 1992, now abandoned, which is a continuation of application No. 07/167,902, filed on Mar. 28, 1988, now abandoned, which is a continuation-in-part of application No. 07/032,800, filed on Mar. 31, 1987, now abandoned.

(51) Int. Cl.$^7$ .............................. A61K 35/16; C07K 1/18; C07K 1/22; C07K 14/755
(52) U.S. Cl. ........................ 530/383; 530/380; 530/413; 530/414; 530/415; 530/416; 435/325; 435/69.6
(58) Field of Search ..................................... 530/383, 380, 530/413, 414, 415, 416; 435/325

(56) References Cited

U.S. PATENT DOCUMENTS 4,670,543  6/1987  Bourgois et al. ..................... 530/383

FOREIGN PATENT DOCUMENTS

| 0 083 483 A1 | 7/1983 | (EP) . |
| 0 131 740 A2 | 1/1985 | (EP) . |
| 0 152 746 | 8/1985 | (EP) . |
| 0 286 323 B1 | 10/1988 | (EP) . |

OTHER PUBLICATIONS

Truett et al., "Characterization of the Polypeptide Composition of Human Factor VIII:C and the Nucleotide Sequence and Expression of the Human Kidney cDNA", DNA 4:333–349 (1985).

Toole et al., "Exploration of Structure–Function Relationships in Human Factor VIII by Site–directed Mutagenesis", Cold Spring Harbor Symposia on Quantitative Biology vol. LI, 543–549 (1986).

Croissant et al., "Characterization of Four Monoclonal Antibodies to Factor VIII Coagulant Protein and Their Use in Immunopurification of Factor VIII", Thrombosis & Haemostasis 56:271–276 (1986).

Eaton et al., Proteolytic Processing of Human Factor VIII. Correlation of Specific Cleavages by Thrombin, Factor Xa, and Activated Protein C with Activation and Inactivation of Factor VIII Coagulant Activity, Biochemistry, 25:505 (1986).

Fulcher et al., "Thrombin Proteolysis of Purified Factor VIII Procoagulant Protein: Correlation of Activation With Generation of a Specific Polypeptide", 1983, Blood 61:807–811 (1983).

Fulcher et al. "Characterization of the human factor VIII procoagulant protein with a heterologous precipitating antibody", Proc. Natl. Acad. Sci USA 79:1648–1652 (1982).

The Merck Index, Tenth Edition (1983) Merck & Co., Inc., Rahway, New Jersey, p. 550 ("3744. Ethylene Glycol").

Goodall et al., "Registry of Monoclonal Antibodies to Factor VIII and von Willebrand Factor", Thromb. Haemostasis 54:878–891 (1985).

Nordfang et al., "Specificity of Monoclonal Antibodies to Factor VIII:C", Thromb. Haemostatis 54:586–590 (1985).

Austen et al., "The Chromatographic Separation of Factor VIII on Aminohexyl Sepharose", Brit. J. Haematol. 43:669–674 (1979).

Griffith et al., "In–process Controls and Characterization of Recombinate™ Antihemophilic Factor (Recombinant)", Proc. 6th Int. Symp. H.T. 27–38 (1990).

Mikaelsson et al., "Preclinical Characterization of Recombinant Factor VIII SQ", XXI International Congress of the World Federation of Hemophilia Mexico City (1994).

Scopes R., "Optimization of Procedures and Following a Recipe", Protein Purification, Principles and Practice, Springer–Verlag, Chapter 7.1 (1982).

Braude, I., "A Simple and Efficient Method for the Purification of Human Gamma Interferon", Preparative Biochemistry 13:177–190 (1983).

Katzmann et al., "Isolation of functional human coagulation Factor V by using a hybridoma antibody", Proc. Natl. Acad. Sci. USA 78:162–166 (1981).

Morgenthaler et al., "Preparation of Virus–Inactivated Factor IX Complex", XXI Congress of the International Society of Haematology, P–TU–132A–8 (1986).

Edwards et al., "Preparation of an Anti–Hemophilic Factor Concentrate With Tri–N–Butylphosphate–Tween 80 and Aminohexyl Sepharose", Fed. Proc. 45:1493 (1986).

Prince et al., "Sterilisation of Hepatitis and HTLV–III Viruses by Exposure to Tri(n–Butyl)phosphate and Sodium Cholate", The Lancet 29 Mar. 706 (1986).

Livingston D., "Immunoaffinity Chromatography of Proteins", Meth. Enzymology 34:723–731 (1974).

Hearn M., "Current Challenges in the Chromatographic Analysis of Biomacromolecules: Can Recent Developments in High Resolution Separation of Peptides and Proteins Provide the Solution for Biotechnology", Chemical Separations, vol. I: Principles, C. Judson King and James D. Navratil, 1986, dr., pp. 77 and 92–93.

(List continued on next page.)

Primary Examiner—Elizabeth C. Kemmerer

(57) ABSTRACT

A process for purifying Factor VIII:C comprising contacting an immobilized antibody specifically binding a Factor VIII:C with Factor VIII:C, desorbing Factor VIII:C from the antibody which had adsorbed it, eluting Factor VIII:C from the presence of the antibody, passing the eluted Factor VIII:C through an affinity region capable of binding the Factor VIII:C, binding the Factor VIII:C in the affinity region and passing contaminants through said region, and eluting the purified Factor VIII:C.

OTHER PUBLICATIONS

Sofer et al., "From R&D to Production: Designing a Chromatographic Purification Scheme", Bio/Technology 5:239–244 (1987).

"A strategy for protein purification", Separation News, Pharmacia, Laboratory Separation Division 13 (6) (1986).

Griffith M., "Biochemical characterization of the Method M AHF process developed to reduce the risk of virus transmission", Proceedings of the Symposium on Biotechnology and the Promise of Pure FVIII Monte Carlo 69–85 (1988).

Hornsey et al., "Immunoaffinity Purification of Factor VIII Complex", Thromb. Haemostasis 57:102–105 (Jan.–Feb. 1987).

Fass et al., "Internal duplication and sequence homology in factors V and VIII", Proc. Natl. Acad. Sci. USA 82:1688–1691 (1985).

Andersson, L.–O., Forsman, N., Huang, K., Larsen, K., Lundin, A., Pavlu, B., Sandberg, H., Sewerin, K., Smart, J., "Isolation and Characterization of Human Factor VIII: Molecular Forms in Commercial Factor VIII Concentrate, Cryoprecipitate, and Plasma", Proc. Nat. Acad. of Sci. U.S.A., vol. 83, pp. 2979–2983, (May 1986).

Bolhuis, P.A., Beeser–Visser, N.H., Sixma, J.J., "Molecular Weight of Human Plasma Factor VIII", Thrombosis Research, vol. 16, pp. 497–506 (1979).

Brinkhous, K.M., Sandberg, H., Garris, J.B., Mattson, C., Palm, M., Griggs, T., Read, M.S., "Purified Human Factor VIII Procoagulant Protein: Comparative Hemostatic Response After Infusions into Hemophilic and von Willebrand Disease Dogs", Proc. Natl. Acad. Sci. USA, vol. 82, pp. 8752–8756, (Dec. 1985).

Dembinski, W.E., Sulkowski, E., "Improved Large Scale Purification Procedure of Natural Human Fibroblast Interferon", Preparative Biochemistry, vol. 16, No. 2 pp. 175–186 (1986).

Eaton, D.L., Vehar, G.A., "Factor VII Structure and Proteolytic Processing" Progress in Hemostasis and Thrombosis, vol. 8: pp. 47–70, (1986).

Tuddenham, E.G.D., Lane, R.S., Rotblat, F., Johnson, A.J., Snape, T.J., Middleton, S., Kernoff, P.B.A., "Response to Infusions of Polyelectrolyte Fractionated Human Factor VIII Concentrate in Human Haemophilia A and von Willebrand's Disease", British J. of Haematology, vol. 52, p. 259–267, (1982).

Fulcher, C.A., Robert, J.R., Holland, L.Z., Zimmerman, T.S., "Human Factor VIII Procoagulant Protein, Monoclonal Antibodies Define Precursor–Product Relationships and Functional Epitopes," J. Clin. Invest., vol. 76, No. 1, pp. 117–124 (Jul. 1985).

Ginsburg, D., Handin, R.I., Bonthron, D.T., Donlon, T.A., Bruns, G.A.P., Latt, S.A., Orkin, S.H., "Human von Willebrand Factor (vWF): Isolation of complemetary DNA (cDNA) Clones and Chromosomal Localization", Science, vol. 228, pp. 1401–1406 (Jun. 21, 1985).

Goding, J.W., "Affinity Chromatograph Using Monoclonal Antibodies", Monoclonal Antibodies: Principles and Practice, Academic Press, Second Edition, pp. 219–240 (1986).

Weiss, H.J., "A Study of the Cation–and pH–Dependent Stability of Factors V and VIII in Plasma", Thromb. Diath. Haemorrh. vol. 14, pp. 32–51, (1965).

Hoyer, L.W., "The Factor VIII Complex: Structure and Function", Blood, vol. 58, No. 1, pp. 1–13, (Jul. 1981).

Köhler, G., Milstein, C., "Continuous Cultures of Fused Cells Secreting Antibody of Predefined Specificity", Nature, vol. 256, pp. 495–497, (Aug. 7, 1975).

Knutson, G.J., Fass, D.N., "Porcine Factor VIII:C Prepared by Affinity Interaction With von Willebrand Factor and Heterologous Antibodies: Sodium Dodecyl Sulfate Polyacrylamide Gel Analysis", Blood, vol. 59, No. 3, pp. 615–624, (Mar. 1982).

Marder, V.J., Mannucci, P.M., Firkin, B.G., Hoyer, L.W., Meyer, D. "Standard Nomenclature for Factor VIII and von Willebrand Factor: A Recommendation by the International Committee on Thrombosis and Haemostasis", Thromb Haemostas, vol. 54, No. 4, pp. 735–907, (Dec., 1985).

Mikaelsson, M.E., Forsman, N., Oswaldsson, U.M., "Human Factor VIII: A Calcium–Linked Protein Complex", Blood, vol. 62, No. 5, pp. 1006–1015, (Nov. 1983).

Toole, J.J., Pittman, D.D., Orr, E.C., Murtha, P., Wasley, L.C., Kaufman, R.J., "A Large Region ($\approx$95 kDa) of Human Factor VIII is Dispensable for In Vitro Procoagulant Activity", Proc. Nat'l Acad. Sci. vol. 83, pp. 5939–5942, (Aug. 1986).

Rotblat, F., Goodall, A.H., O'Brien, P., Hawlings, F., Middleton, S., "Monoclonal Antibodies to Human Procoagulant Factor VIII", J. Lab. Clin. Med., vol. 101, No. 5, pp. 736–746, (May 1983).

Scopes, R., Protein Purification Principles and Practice, Springer Verlag New York Heidelberg Berlin, (1982).

Shinowara, G.Y., "Kinetic Studies on the Thermal Denaturation of Human Antihemophilic globulin (AHG)", Fourteenth Annual Symposium on Blood, pp. 636–637, (1966).

Stibbe, J., Hemkke, H.C., Creveld, S.v., "The Inactivation of Factor VIII In Vitro", Thromb. Diath. Haemorrh., vol. 27, No. 1, pp. 43–58, (Feb. 29, 1972).

Toole, J.J., Knopf, J.L., Wozney, J.M., Sultzman, L.A., Buecker, J.L., Pittman, D.D., Kaufman, R.J., Brown, E., Shoemaker, C., Orr, E.C., Amphlett, G.W., Foster, W.B., Coe, M.L., Knutson, G.J., Fass, D.N., Hewick, R.M., "Molecular Cloning of a cDNA Encoding Human Antihaemphilic Factor", Nature, vol. 312, pp. 342–347, (Nov. 22, 1984).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 30–36 and 38–39 is confirmed.

Claims 14 and 37 are cancelled.

Claim 1 is determined to be patentable as amended.

Claims 2–13 and 15–29, dependent on an amended claim, are determined to be patentable.

New claims 40–46 are added and determined to be patentable.

1. A method of purifying Factor VIII:C from a mixture of polypeptides and contaminants comprising:
   (a) adsorbing an antibody to a matrix to form an immunoaffinity matrix, which antibody binds by hydrophobic attraction to the Factor VIII:C to be purified to form hydrophobic bonds, adding the mixture to said antibody before or after said antibody is bound to the matrix, thereby adsorbing said Factor VIII:C in the immunoaffinity matrix;
   (b) eluting the Factor VIII:C from the immobilized antibody by treating the Factor VIII:C:immunoaffinity matrix with a desorbing substance which breaks the hydrophobic bonds between the Factor VIII:C and the immobilized antibody to desorb the Factor VIII:C from said matrix [wherein the desorbing substance is a non-polar agent in a buffered salt solution];
   (c) *then* passing the Factor VIII:C to be purified through an affinity region which is an ion-exchange region capable of binding to the Factor VIII:C, thereby binding the Factor VIII:C to the affinity material while allowing the contaminants to pass through the affinity region, *wherein the desorbing substance in step (b) is a non-polar agent in a buffered salt solution and said desorbing substance has an ionic strength that permits the Factor VIII:C desorbed in step (b) to bind the ion-exchange region of step (c) without prior desalting*; and
   (d) eluting the purified Factor VIII:C from the affinity region.

40. *A method of purifying Factor VIII:C from a mixture of polypeptides and contaminants comprising:*
   *(a) adsorbing an antibody to a matrix to form an immunoaffinity matrix, which antibody binds by hydrophobic attraction to the Factor VIII:C to be purified to form hydrophobic bonds, adding the mixture to said antibody before or after said antibody is bound to the matrix, thereby adsorbing said Factor VIII:C in the immunoaffinity matrix;*
   *(b) eluting the Factor VIII:C from the immobilized antibody by treating the Factor VIII:C:immunoaffinity matrix with a desorbing substance which breaks the hydrophobic bonds between the Factor VIII:C and the immobilized antibody to desorb the Factor VIII:C from said matrix, wherein the desorbing substance is a non-polar agent in a buffered salt solution having a low ionic strength;*
   *(c) then passing the Factor VIII:C to be purified through an affinity region which is an ion-exchange region capable of binding to the Factor VIII:C, thereby binding the Factor VIII:C to the affinity material while allowing the contaminants to pass through the affinity region; and*
   *(d) eluting the purified Factor VIII:C from the affinity region.*

41. *The method of claim 40 wherein said mixture of polypeptides is present in a cell culture media derived from recombinant DNA technology.*

42. *A method according to claim 40 wherein said antibody is monoclonal.*

43. *The method of claim 40 wherein said nonpolar agent is ethylene glycol or propylene glycol.*

44. *The method of claim 43 wherein said nonpolar agent is ethylene glycol.*

45. *The method of claim 40 wherein a virus-inactivating step is employed.*

46. *The method of claim 40 wherein said mixture of polypeptides is present in a cell culture media derived from recombinant DNA technology, said antibody is monoclonal, and said nonpolar agent is ethylene glycol.*

* * * * *